(12) United States Patent
Ackermann et al.

(10) Patent No.: US 7,349,856 B2
(45) Date of Patent: Mar. 25, 2008

(54) METHOD FOR SELECTIVELY ENABLING OR BLOCKING THE USE OF MEDICAL EQUIPMENT

(75) Inventors: Rudolf Ackermann, Buckenhof (DE); Hans Huebsch, Erlangen (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1114 days.

(21) Appl. No.: 10/208,466

(22) Filed: Jul. 29, 2002

(65) Prior Publication Data

US 2003/0023460 A1    Jan. 30, 2003

(30) Foreign Application Priority Data

Jul. 30, 2001  (DE) ................. 101 37 244
May 7, 2002   (DE) ................. 102 20 348

(51) Int. Cl.
*G06Q 10/00* (2006.01)
*G06Q 50/00* (2006.01)

(52) U.S. Cl. ................. 705/2; 705/3; 705/75
(58) Field of Classification Search ............... 705/2–4, 705/75; 700/36; 600/300
See application file for complete search history.

(56) References Cited

U.S. PATENT DOCUMENTS 5,258,906 A * 11/1993 Kroll et al. ............... 705/2
6,829,704 B2 * 12/2004 Zhang et al. .............. 713/1
6,966,000 B2 * 11/2005 Zhang et al. ............ 726/22
6,983,375 B2 * 1/2006 Zhang et al. ............ 726/35
7,103,578 B2 * 9/2006 Beck et al. .............. 705/75

FOREIGN PATENT DOCUMENTS

| DE | 41 20 110    | 12/1992 |
| DE | 43 38 240    | 5/1995  |
| DE | OS 199 15 671| 10/2000 |
| FR | 2 776 8181   | 3/1998  |
| WO | WO 01/17450  | 3/2001  |
| WO | WO 01/18616  | 3/2001  |

OTHER PUBLICATIONS

"Problems With COTS Software: A Case Study," Beheshti et al, HTTP:/www.slis.ualberta.ca/cais2000/beheshti.htm, Feb. 22, 2002.
Patent Abstracts of Japan Publication No. 2001160106 for Japanese Application No. 20000255632.

* cited by examiner

*Primary Examiner*—C. Luke Gilligan
(74) *Attorney, Agent, or Firm*—Schiff Hardin LLP

(57) ABSTRACT

In a method for selectively enabling or blocking the use of medical equipment made available by a vendor or a system option in the medical equipment, for a customer, wherein the equipment is arranged in a facility of the customer, a compilation is created and stored at a vendor's computer from which it proceeds whether the customer is permitted to use the medical equipment overall or which system option of the medical equipment the customer is permitted to use. Given a desired utilization of the medical equipment or a system option of the medical equipment by the customer, a check is made at the vendor's computer as to see whether the customer is authorized for the use and whether costs arising from previous use are to be paid. The use is automatically enabled when the authorization still exists and no costs are outstanding, or the use is automatically inhibited when there is no authorization or costs are still outstanding.

17 Claims, 5 Drawing Sheets

METHOD FOR SELECTIVELY ENABLING OR BLOCKING THE USE OF MEDICAL EQUIPMENT

BACKGROUND OF THE INVENTION

1. Field of the Invention

The present invention is directed to a method for selectively enabling or blocking the use of medical equipment arranged in a facility of a customer.

2. Description of the Prior Art

High-performance medical equipment, i.e. medical systems, installations and devices such as magnetic resonance apparatuses, X-ray computed tomography systems, X-ray systems, ultrasound devices or lithotriptors, as well as system options of such medical equipment in the form of specific hardware configurations or application software are usually relatively expensive to acquire and therefore represent a capital investment. For a potential customer of one of these systems, for example a radiologist, it is often very difficult to estimate whether a profitable return on the investment can be expected. Many customers of such medical equipment therefore avoid the capital investment, particularly for new system options of the medical equipment. This results in a loss to patients of the benefit of the diagnostic and therapeutic advantages that such new system options provide. Moreover, technological advances in medical technology may be impeded due to the lack of market penetration on the part of the users.

Published Japanese Application 2001160106 discloses a method and a system for leasing a medical treatment equipment by a customer so that the customer need not purchase the medical treatment equipment. The utilizations of the treatment equipment are registered, stored, and the costs for the utilizations of the treatment equipment are calculated and billed to the customer.

German OS 43 38 240 discloses a dental apparatus that a vendor offers to a customer in a ready-to-use form in return for payment. The apparatus contains a control device that activates and deactivates the apparatus for a specific job performance. The activation of the control device and the enablement of the performance ensue by means of a data carrier. The data carrier can be a diskette or a magnetic card or laser card. The enablement of the performance also can ensue by data transmission via a telephone line by modem.

PCT Applications WO 01/17450 and WO 01/18616 disclose equipment for treating tissue that include a controller, a reader device and a memory card. The memory card has a memory containing an identification code that can be read by the reader device and communicated to the controller. Based on the identification code, the controller either enables or blocks the use of the equipment.

Published French Application 2 776 818 discloses a method wherein medical equipment is provided with an identification number that can be electronically read and communicated to a computer. The prior utilization of the medical equipment can be replicated on the basis of the identification number.

German OS 41 20 110 discloses a telecommunication device with which the fee units per use can be decentrally stored in a user-related manner.

SUMMARY OF THE INVENTION

An object of the present invention is to provide a computerized method with which a vendor of medical equipment of the type initially described is able to make the equipment available to a potential customer such that the commercial interests of the vendor are preserved without directly involving high investment costs for the customer.

This object is inventively achieved in a method for selectively enabling or blocking the use of medical equipment made available by a vendor or a system option in the medical equipment, for a customer wherein the medical equipment is arranged in a facility of the customer, wherein a computer device of the medical equipment at the customer is connectable via a communication network to a computer device of the vendor. The vendor's computer device contains a compilation from which it proceeds whether the customer is permitted to use the medical equipment overall, or which system option of the medical equipment the customer is permitted to use, and to what extent the customer is permitted to use the medical equipment or the system option. When the customer intends to use the medical equipment or the system option, a connection between the computer device of the medical equipment and the computer device of the vendor is established via the communication network by means of the computer device of the medical equipment, and usage data are communicated to the computer device of the vendor by means of the computer device of the medical equipment. Based on the usage data, the computer device of the vendor reviews whether the customer is authorized for the intended use based on the compilation. This review with the vendor's computer device includes a determination of the cost or accumulated costs of one or more previous uses of the medical equipment or the system option have been reconciled or paid. Based on the review, an automatic enablement of the use ensues by sending enablement data by means of the vendor's computer device to the computer device of the medical equipment via the communication network when the utilization authority exists and no unpaid costs are outstanding, or automatic inhibiting of the use ensues by sending blocking data by means of the vendor's computer device to the computer device of the medical equipment via the communication network when there is no authorization or unpaid costs are still outstanding.

The inventive method allows a vendor of medical equipment to make the medical equipment available for use to a customer under the vendor's control, so the customer need not purchase the medical equipment but only pays an agreed price to the vendor for the respective, intended utilization. The agreement between the vendor and the customer also can be such that the customer purchases the medical equipment in a specific configuration and the vendor makes additional system options in the form of hardware or software applications available, the customer only paying for these when the customer uses them. The customer thus need not purchase these additional system options. In this way, the customer can reduce his investment risk, particularly with respect to new and expensive system options, and the vendor of the medical equipment receives an adequate remuneration for making the medical equipment or a specific system option available. With the inventive method, the vendor has the possibility of automatically blocking the use of the entire medical equipment or a system option of the medical equipment, so the vendor has control over usage by customers having, for example, expired authorizations or past due accounts. This method thus creates the possibility of making especially expensive system options available to a customer without immediate financial outlay for the customer. In this way, the customer's willingness to test system options that are expensive to acquire is promoted, and as a result patients receive the diagnostic or therapeutic benefits associated therewith and technological progress is promoted by the exchange between the customer and the vendor regarding advantages and disadvantages of the system options.

The enablement or the blockage of the use of the medical equipment or a system option of the medical equipment preferably ensues via an online connection between the computer device of the medical equipment and the computer device of the vendor or by e-mail with which, for example, an enable or inhibit code is communicated from the computer device of the vendor to the computer device of the medical equipment.

In an embodiment of the invention each use of the medical equipment or a system option of the medical equipment is registered by the computer device of the vendor, so that whether the customer's use authorization is still in force can be checked before each use of the medical equipment or a system option of the medical equipment.

According to one version of the invention, the customer can acquire the authorization for a specific number of uses of the medical equipment or a system option of the medical equipment. According to another version, the use of the medical equipment or a system option of the medical equipment is automatically blocked when the customer has consumed the number of uses that the customer acquired. The customer thus has the possibility of purchasing a specific package of uses. If it turns out for the customer that, for example, a particular system option does not provide the effect the customer desired in diagnosis or therapy, then the customer simply can refrain from further purchasing of the system option without suffering a great financial hardship. When, in contrast, the utilization of a system option proves positive, then the customer can re-purchase this option.

In another embodiment of the invention the customer can purchase the usage authorization of the medical equipment or a system option of the medical equipment for a specific time duration. In one version of the invention, the use of the medical equipment or a system option of the medical equipment can be automatically blocked when the time duration purchased for the use has elapsed. In this way, the customer has the possibility of, for example, testing a system option over a certain time span without great financial outlay. If it turns out that the system option yields no advantages for the customer, the customer can refrain from extending the time duration. If the system option proves positive for the customer's applications, the customer can undertake further extension of the time duration for the system option.

Particularly for this form of paying for the use of medical equipment or a system option of the medical equipment, in a further version of the invention the system time of the medical equipment is monitored by the computer device of the vendor by interrogation via the communication network in order to be able to register potential manipulations of the system time by the customer in order to extend the use duration of the medical equipment or the system option and thus a financial loss on the part of the vendor is avoided. As used herein "system time" means the time kept within the medical equipment, this usually being adjustable.

In another embodiment of the invention the customer is extended a credit for the use of the medical equipment or a system option of the medical equipment. Accordingly, the customer can make use of the medical equipment or a system option in the framework of the credit that has been extended. When the customer exceeds the scope of the credit by virtue of the customer failing to follow a payment plan for reducing the credit, the use of the medical equipment or the system option is blocked until the costs that have accumulated have been paid and the customer is again within the customer's credit limit.

According to a further version of the invention, a check is made at certain times as to whether the costs that have accumulated for the customer are due, and the use of the medical equipment or a system option is blocked until the costs have been paid.

In a further version of the invention, the computer device of the medical equipment sends accounting data for payment of accumulated costs—whether from a purchased number of uses, a specific time duration of the use, or extended credit—to the vendor's computer device, and the vendor's computer device automatically charges a customer account and, after charging the account, communicates a receipt to the computer device of the medical equipment of the customer. Thus, an automated billing and charging of the customer account is advantageously utilized, so that the organizational outlay for invoicing the services is reduced.

As mentioned, the computer device of the medical equipment and the vendor's computer device communicate with one another via a communication network. If communication problems arise between the vendor's computer device and the computer device of the medical equipment, in a further version of the invention the communication of usage data and data for enabling or blocking the use of the medical equipment or a system option ensue repeatedly after certain time intervals. Such a time interval preferably amounts to only a few minutes.

For ensuring security of the data against misuse by third parties, the usage data or the data for enabling or blocking the use of the medical equipment or a system option are communicated in encrypted or signed form between the computer device of the medical equipment and the vendor's computer device.

In another version of the invention the costs to be paid for the use are graduated dependent on the use of the medical equipment or a system option, so that a customer—for instance beyond a specific number of uses or beyond a specific time duration of a use—can obtain a more beneficial price for the use of the medical equipment or a system option.

In a further embodiment of the invention, examination-specific data are communicated from the medical equipment to the vendor's computer device in addition to the usage data. This is particularly required if the vendor is to prepare a detailed invoice for the customer for the use of the medical equipment or a system option, which the customer needs, for example, for submission to financial authorities.

DESCRIPTION OF THE PREFERRED EMBODIMENTS

Figure 1:
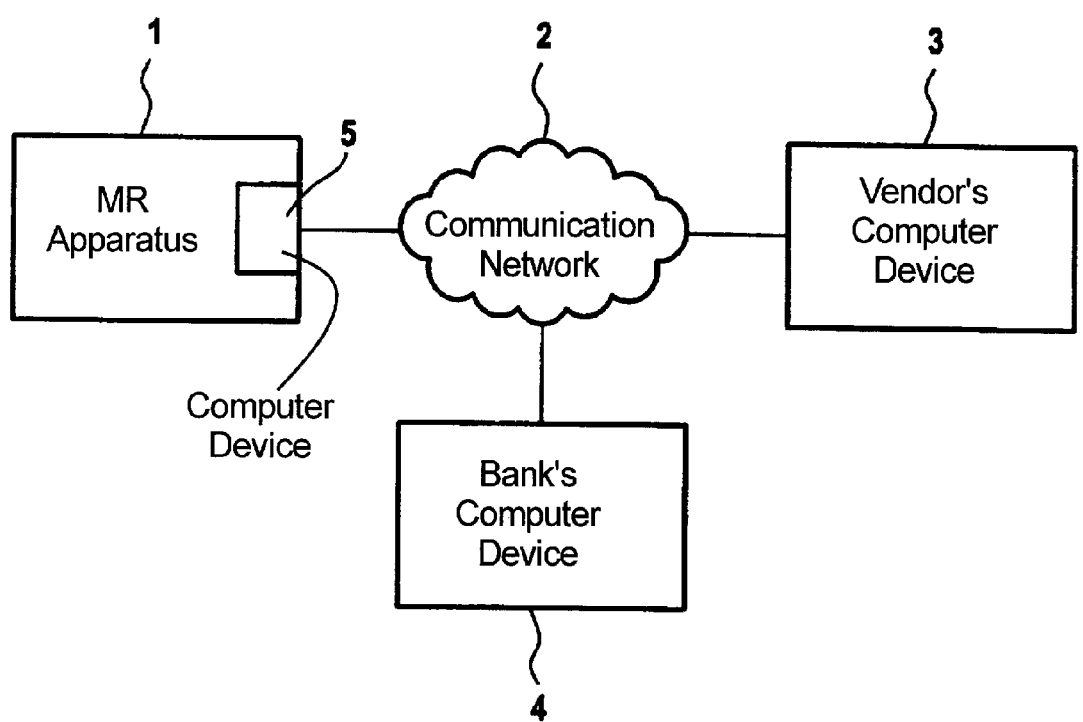
FIG. 1 illustrates a magnetic resonance apparatus connected to a communication network and a computer device of a vendor of the magnetic resonance apparatus connected to the communication network for implementing the inventive method.

In a block diagram, FIG. 1 shows medical equipment in the form of a magnetic resonance apparatus 1 that has a computer device 6 that is connected to a communication network 2 in the schematically indicated way. A computer device 3 of a vendor of the magnetic resonance apparatus 1, for example a manufacturer, importer or some other distributor of the magnetic resonance apparatus 1, also is connected to the communication network 2. The magnetic resonance apparatus 1 is arranged in a facility (not shown in detail) of a customer of the vendor, for example in a clinic or in a medical practice. The vendor's computer device 3 is geographically and spatially separated therefrom in a facility of the vendor. The communication network 2 is preferably a public and freely accessible communication network, for example the Internet, via which a connection can be set up in a known way between the computer device 5 of the magnetic resonance apparatus 1 and the computer device 3.

The structure shown in FIG. 1 represents a platform for the implementation of the inventive method, whereby the intended use of the overall magnetic resonance apparatus 1 or of one or more system options of the magnetic resonance apparatus 1 is enabled or blocked for the customer dependent on conditions that are explained below.

The basis for such an enterprise is usually an agreement concluded between the customer and the vendor of the magnetic resonance apparatus 1 wherein the conditions and the scope of use by the customer of the magnetic resonance apparatus 1 or a system option of the magnetic resonance apparatus 1 in return for payment are defined. In order to be able to use the magnetic resonance apparatus 1, thus, the customer need not purchase the entire device but uses a contract with the vendor to define a use of the magnetic resonance apparatus 1 or individual system options of the magnetic resonance apparatus 1 in return for payment. In the exemplary embodiment, the invention is explained on the basis of a contractual agreement governing the use of a number of system options, for example a specific set of coils of the magnetic resonance apparatus 1 or a software option for imaging with the magnetic resonance apparatus 1. Below, such a system option covered by the contract is referred to as a "pay-per-use" system option (PPU system option). In the present instance, the contract between the customer and the vendor covers three such PPU system options, PPU-SO1 through PPU-SO3, however, the contract also could govern the use of the overall magnetic resonance apparatus 1.

Figure 2:
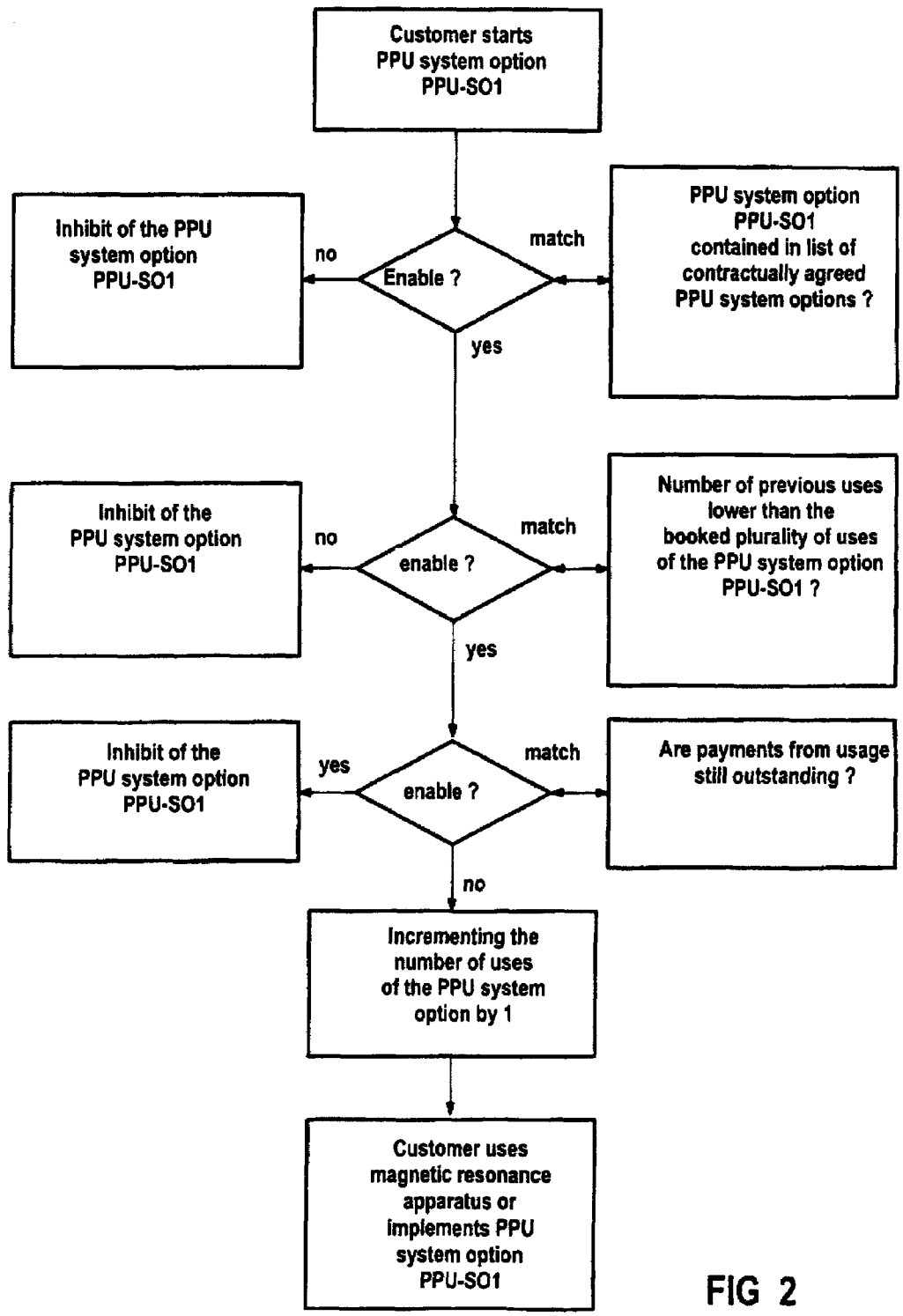
FIGS. 2-4 are flowcharts for explaining the inventive method.

According to a first embodiment of the contract, the customer can acquire the authorization for a specific number of uses of the PPU system options PPU-SO1 through PPU-SO3 of the magnetic resonance apparatus 1 for a specific sum. According to such a contractual agreement, a compilation is prepared that reveals how many times the customer can use which PPU system options—the PPU system options PPU-SO1 through PPU-SO3 in the present case. When, for example in the framework of an examination of a patient, a customer starts the PPU system options PPU-SO1, then a check is first made—as shown in FIG. 2—as to whether the PPU system option PPU-SO1 is covered by the contract. A comparison to the compilation that contains all PPU system options PPU-SO1 through PPU-SO3 contractually agreed upon between the customer and the vendor ensues for this purpose. If the PPU system option PPU-SO1 is not a constituent of the list, i.e. was not included in the contract, the customer would fundamentally not be authorized to use this PPU system option PPU-SO1. The use of this PPU system option PPU-SO1, accordingly is automatically blocked. When, in contrast, the PPU system option is a part of the contract, this being true in the present case, then the customer is authorized to use the PPU system option PPU-SO1.

In a second step, a check is made on the basis of the compilation as to whether the number of uses of the PPU system option PPU-SO1 contracted by the customer has already been used. If so, then the customer is no longer authorized to use the PPU system option PPU-SO1 and the use of the PPU system option PPU-SO1 would be automatically blocked for the customer. In a further step, a check is made before enablement of the PPU system option PPU-SO1 as to whether costs incurred by the customer, for example deriving from an earlier contract governing the use of the PPU system options PPU-SO1 through PPU-SO3, have accumulated that have not yet been reconciled. If this were the case, the use of the PPU system option PPU-SO1 would be automatically blocked for the customer until the customer has paid the costs. Otherwise, as in the case of the exemplary embodiment, the number of uses of the PPU system option PPU-SO1 is incremented by one by a usage counter and stored, and the use of the PPU system option PPU-SO1 is automatically enabled for the customer.

This method for enabling a use always is repeated when the customer would like to use one of the system options PPU-SO1 through PPU-SO3 classified as PPU system option.

The check as to whether the PPU system option the customer for use is a part of the contract between the customer and the vendor of the magnetic resonance apparatus 1, i.e. the comparison to the compilation of contractually agreed PPU system options, the check on the basis of the compilation as to whether the customer is still authorized to use the PPU system option, the check as to whether costs are still due from the customer, as well as the automatic enabling or the automatic blocking of the use are undertaken by the computer device 3 of the vendor of the magnetic resonance apparatus 1. Whenever a PPU system option is to be employed, the computer device 5 of the magnetic resonance apparatus 1 sets up a communication connection to the vendor's computer device 3 via the communication network 2, so that the comparison to the compilation of the PPU system options available to the customer and the comparison to the number of prior uses of the individual PPU system options can ensue. The compilation is stored in a datafile accessible by the computer device 3. The computer device 5 of the magnetic resonance apparatus 1 communicates usage data containing particulars about the PPU system option to be checked as well as (if necessary) particulars about the type of examination or particulars about the prior usage of the PPU system option to the vendor's computer device 3. The vendor's computer device 3 is able to determine the authorization of the customer to use the system option therefrom on the basis of the compilation that contains data about previous usage and data about the contractual agreement. Before enabling the PPU system option, the vendor's computer device 3 also checks whether costs to be paid by the customer have accumulated, for example arising from an earlier contract governing the use of the PPU system options PPU-SO1 through PPU-SO3. When the check by the vendor's computer device 3 shows that the customer is authorized to use the desired system option and that no costs have accumulated for the customer from the use of the PPU system options PPU-SO1 through PPU-SO3 that are still to be paid, then the vendor's computer device 3 sends an enable code to the computer device 5 of the magnetic resonance apparatus 1, so that the desired PPU system option can be enabled for use by the customer. If the customer is no longer authorized to use the desired PPU system option, for example because the number of purchased uses has been consumed or costs that accumulated from the usage have not yet been paid, the vendor's computer device 3 sends an inhibit code to the computer device 5 of the magnetic resonance apparatus 1, so hat the desired PPU system option cannot be enabled for use by the customer. The customer cannot recognize whether the communicated code is an enable code or inhibit code, so that manipulations on the part of the customer to generate an enable code from an inhibit code are precluded.

If, following an automatic inhibit of a PPU system option, the customer would like to obtain enablement, the customer must either again purchase a specific number of uses, i.e. undertake a re-booking of the desired PPU system option, or pay any past due costs that have accumulated from the usage. A re-booking of a PPU system option can, for example, ensue on the basis of an e-mail from the computer device 5 of the magnetic resonance apparatus 1 to the vendor's computer device 3.

The data transfer between the computer device 5 of the magnetic resonance apparatus 1 and the vendor's computer device 3, which covers usage data of the magnetic resonance apparatus 1, as well as data for enabling and for blocking the use of the PPU system options of the magnetic resonance apparatus 1, ensue in encrypted or signed form, so that security of the data against misuse by third parties is assured. Well-known methods are employed for the encryption or the signature. Particularly when the check of the authorization to use PPU system options as well as the enabling and the blocking of the use are performed by the vendor's computer device 3, the communication of the usage data and the data for enabling or for blocking the use repeat after specific time intervals, usually amounting to a few minutes, in the event of communication problems between the vendor's computer device 3 and the computer device 5 of the magnetic resonance apparatus 1.

According to a second embodiment of the contract, the customer can acquire the authorization to use the PPU system options PPU-SO1 through PPU-SO3 for a specific time duration, for example a week, a month or a year. Differing from the first flowchart shown in FIG. 2 and as proceeds from the flowchart shown in FIG. 3, a check is made in this case in the second step as to whether the booked time span for the use of the PPU system option PPU-SO1 has already expired. If the time duration over which the customer was authorized to use the PPU system option PPU-SO1 has elapsed, the use of the PPU system option PPU-SO1 is automatically blocked. Otherwise, the use of the PPU system option PPU-SO1 is automatically enabled for the customer, insofar as no accumulated costs remain to be paid.

The check of the authorization to use the PPU system option on the basis of the compilation containing data about the contractually agreed PPU system options as well as about the contractually agree usage duration, the check as to whether costs to be paid have accumulated, as well as the enabling and the blocking of the use, again ensue by means of the computer device 3 of the vendor of the magnetic resonance apparatus 1. Data are correspondingly transferred between the computer device 5 of the magnetic resonance apparatus 1 and the vendor's computer device 3 via the communication network 2 in the way that has already been described.

Given this form of contract, the computer device 3 monitors the system time of the magnetic resonance apparatus 1, i.e. the internally kept time, at least by spot checks in the exemplary embodiment, particularly when the expiration of the contractually agreed time for the use of the PPU system options is approaching. This can occur best by setting up an online connection between the computer devices 3 and 5, so that the vendor's computer device 3 can check the system time of the magnetic resonance apparatus 1. Potential manipulations of the system time performed by the customer, for example by resetting the system time, which would to a lengthening of the usage duration of the PPU system options given a calculation of the use duration based on the system time of the magnetic resonance apparatus 1, can be recognized and dealt with in this way.

According to a third embodiment of the contract, the customer can acquire the authorization to use the PPU system options PPU-SO1 through PPU-SO3 of the magnetic resonance apparatus 1 on a credit basis, with the scope of the credit being contractually defined.

Figure 4:
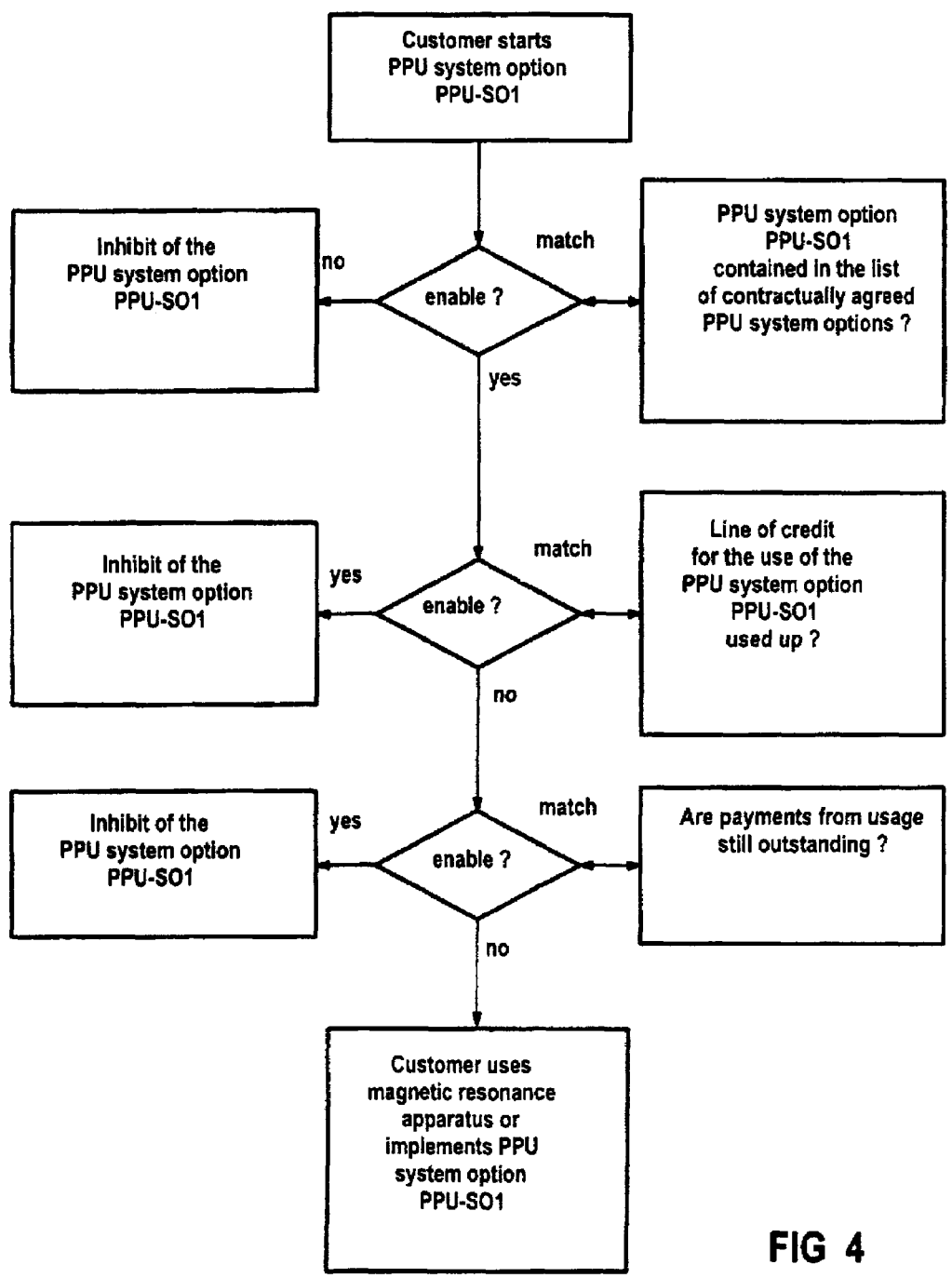

As shown in FIG. 4, a check follows in the second step as to whether the customer has already exhausted the credit limit agreed upon for each PPU system option PPU-SO1 through PPU-SO3. If this is the case, the use of the respectively affected PPU system option of the magnetic resonance apparatus 1 is blocked until the customer has paid the costs that have accumulated. When, in contrast, the customer is still within the credit limit for the corresponding PPU system options PPU-SO1 through PPU-SO3, the use of the respective PPU system option is enabled for the customer. In this form of contract, as well, the check of the authorization of the customer to use the PPU system options PPU-SO1 through PPU-SO3 covered by the contract on the basis of the compilation containing data about the contractually agreed PPU system options as well as about the credit limit, as well as the enabling and the blocking of the use of the PPU system options ensue by means of the vendor's computer device 3.

When the credit limit of the customer is exhausted for individual or for all PPU system options covered by the contract, then the computer device 5 of the magnetic resonance apparatus 1—prompted by the customer—sends accounting data containing, for example, the account number as well as, preferably, an authorization of the customer to the vendor's computer device 3, so that the vendor's computer device 3 can automatically charge a customer's account and communicate a corresponding receipt to the magnetic resonance apparatus 1 of the customer. Such an accounting method is schematically illustrated in FIG. 1, whereby the vendor can set up a connection via the communication network 2 to a computer device 4 of a bank at which the customer maintains an account and can initiate corresponding booking measures with the authorization of the customer.

Figure 3:
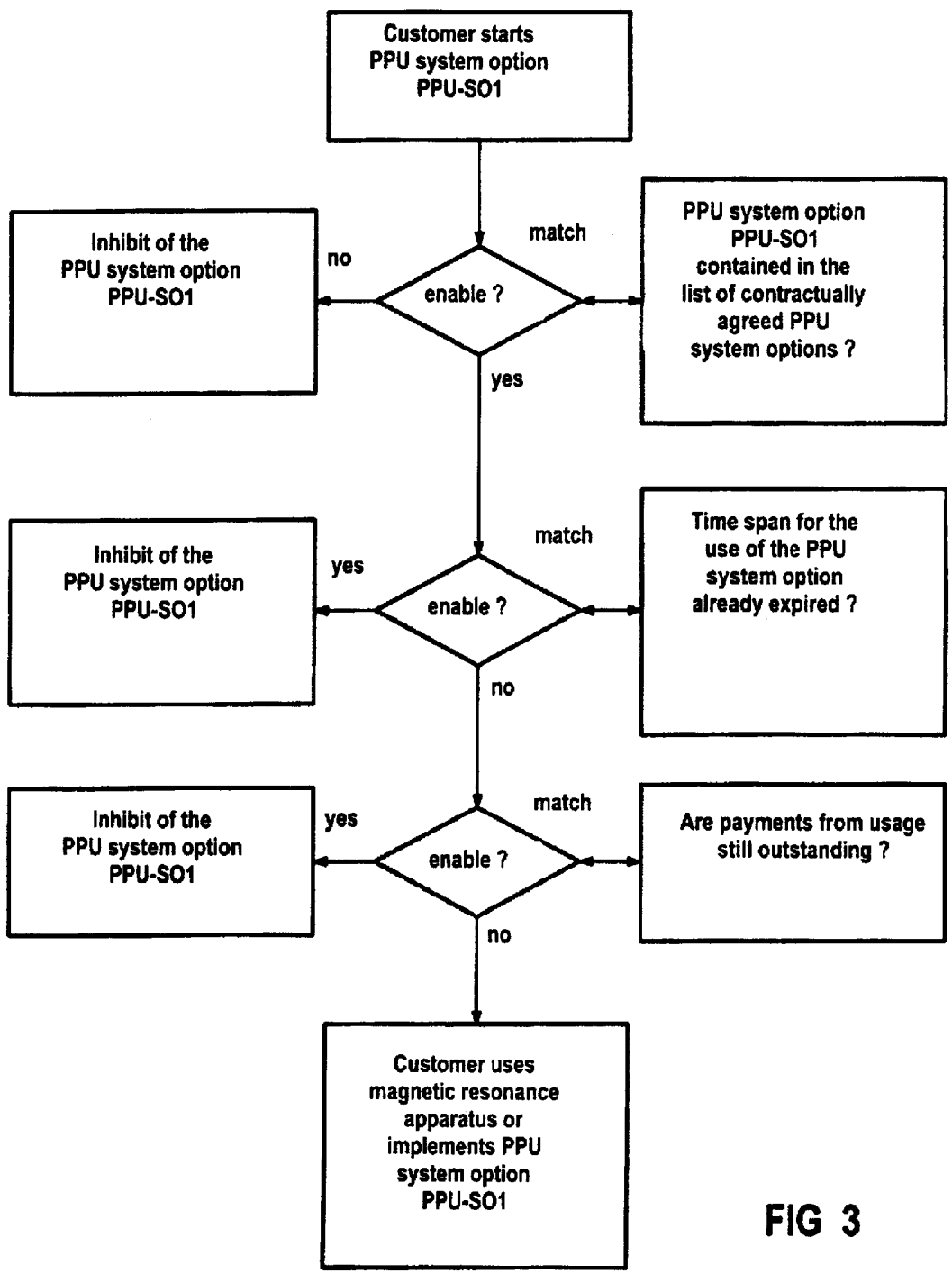

Moreover, the payment of accumulated costs also can ensue in this way in the exemplary embodiments illustrated on the basis of FIGS. 2 and 3.

The payment of the accumulated costs, however, need not necessarily be automated in this way. The customer alternatively can pay the accumulated costs in a conventional way, for example by means of instructions to the bank to initiate the extension of a further credit limit, with an answerback to the vendor.

Figure 5:
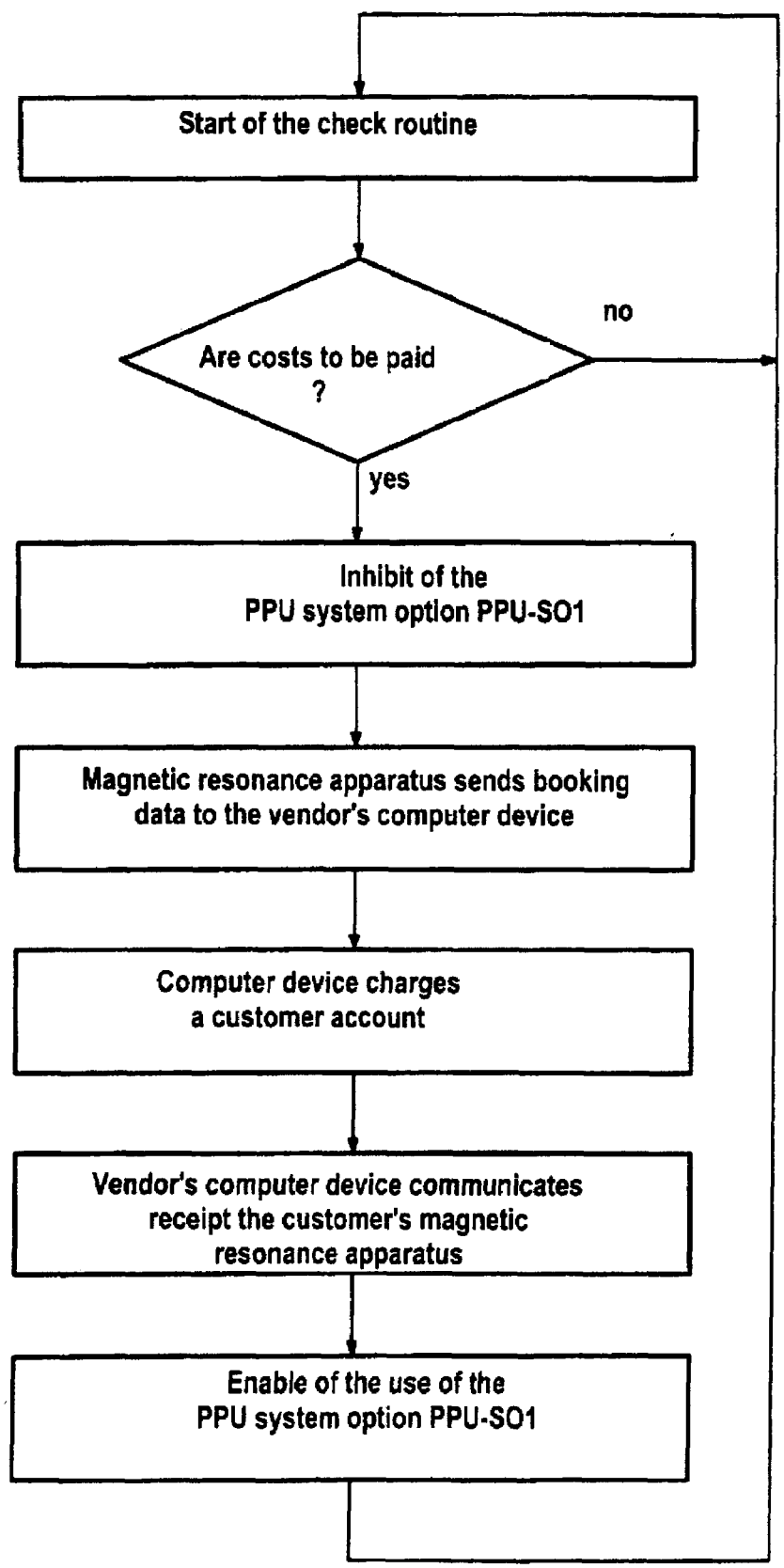
FIG. 5 is a flowchart of a check routine for use in the inventive method.

The accounting for the use of the PPU system options PPU-SO1 through PPU-SO1, however, can also ensue as shown in FIG. 5. At certain times, for example daily or weekly, a check routine is started on the vendor's computer device 3 that checks how often the customer has used which of the PPU system options PPU-SO1 through PPU-SO3 and whether costs that accumulated over the acquired number of uses are due, and/or whether the agreed upon time duration for the use has expired and/or whether the line of credit of the customer under the contract has been exceeded. When, for example, costs for the PPU system option PPU-SO1 that exceed the agreed credit limit for the use of the PPU system option PPU-SO1 have been incurred or when the purchased plurality for the use of the system option PPU-SO1 has been used up or when the time duration for the used of the PPU system option PPU-SO1 has expired, the PPU system option PPU-SO1 remains blocked, regardless of a desired use of the PPU system option PPU-SO1 by the customer, until the computer device 5 of the magnetic resonance apparatus 1 has communicated accounting data to the computer device 3—preferably after having been prompted by the vendor's computer device 3—that allow the vendor to charge an account of the customer. The inhibit is registered in the compilation for the customer, so that, given a requested use of the PPU system option which ensues a check to be made as to whether accumulated costs have been paid, the computer device 3 does not enable this use. After charging the customer's account, the vendor's computer device 3 sends a receipt to the computer device 5 of the magnetic resonance apparatus 1 of the customer, and the PPU system option PPU-SO1 is re-enabled for the customer, i.e. the inhibit is deleted from the compilation, so that the PPU system option PPU-SO1 can in turn be enabled by communication of an enable code when the customer wants to use this PPU system option PPU-SO1.

According to special contractual agreements that can be applied to all three forms of the contract, the costs to be paid for a use can be graduated dependent on the usage of the magnetic resonance apparatus 1 or of the PPU system options PPU-SO1 through PPU-SO3. When, for example, the customer uses the PPU system option PPU-SO1 especially often, the price for the use of this PPU system option is reduced by a defined amount. A multiple graduation can be provided. For example, the price per use can be reduced when the customer uses a PPU option more than 50 times, more than 100 times, more than 150 times, etc., within a specific time span.

In all three versions of the contract the computer device 5 of the magnetic resonance apparatus 1 can communicate examination-specific data to the computer device 3 of the vendor in addition to the usage data, so that the vendor can prepare a detailed invoice for the customer as the customer may need, for example, for submission to financial authorities. As was the case in the communication of the usage data as well as the data for enabling or blocking of the use, the data transfer ensues in encrypted or signed form via the communication network 2 in order to assure data security. Among other things, the examination-specific data cover the name of the patient, the time of day of the examination, the date of the examination as well as the type and form of examination.

The contractual agreement between a vendor and a customer, moreover, need not be limited to one type of contract. Mixed forms of the described contract types are possible. For example, a specific number of uses for the PPU system option PPU-SO1, a specific time duration for using the PPU system option PPU-SO2, a specific line of credit for using the PPU system option PPU-SO3 can be agreed between the vendor and the customer. Advantageously, special conditions for the customer, for example a specific number of free uses of the medical equipment or of a system option of the medical equipment, can be part of the contract.

Further, the contractual agreement can be of such a nature that each use of the magnetic resonance apparatus 1 or of a PPU system option of the magnetic resonance apparatus 1 is immediately invoiced and paid for.

The data transfer between the computer device 5 of the magnetic resonance apparatus 1 and the vendor's computer device 3 need not necessarily ensue via the Internet but can alternatively ensue over some other network or communication means in a known way.

The medical equipment, moreover, need not necessarily be a magnetic resonance apparatus but can also be an X-ray computed tomography apparatus, an X-ray installation, an ultrasound device, a lithotriptor or some other medical device, system, hardware or software system.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for selectively enabling or blocking usage of a medical implement selected from the group consisting of medical equipment and a system option in said medical equipment, comprising the steps of:

for a customer of a vendor of said medical implement, said customer having a facility at which said medical implement is located, storing a compilation at a computer of said vendor which designates a usage level of said customer indicting whether said customer is permitted to use said medical implement and whether said customer is restricted to use said medical implement only to an extent that is less than unrestricted, complete use of said medical implement;

when said customer desires to use said medical implement, establishing communication between a computer of said medical implement and said computer of said vendor and communicating usage data from said computer of said medical implement to said computer of said vendor;

based on said usage data, reviewing said compilation at said computer of said vendor to determine whether said customer is authorized to use said medical implement;

additionally reviewing, dependent on said compilation at said computer of said vendor, whether said customer has an economic relationship with said vendor consistent with said usage level for use of said medical implement; and automatically enabling said use of said medical implement by said customer according to said usage level by communicating enabling data from said computer of said vendor to said computer of said medical implement when, based on said review, said authorization and said economic relationship exist, and automatically communicating blocking data from said computer of said vendor to said computer of said medical implement that automatically blocks usage of said medical implement by said customer if, based on said review, either of said authorization or said economic status does not exist.

2. A method as claimed in claim 1 wherein the step of reviewing whether said economic relationship exists between said customer and said vendor permitting said use by said customer of said medical implement comprises reviewing accumulated costs for said use of said medial implement in said compilation, and determining, at the time said usage data are communicated whether said costs have been paid by said customer.

3. A method as claimed in claim 1 comprising registering, in said compilation, each use of said medical implement by said customer.

4. A method as claimed in claim 1 comprising establishing an account between said customer and said vendor wherein said customer can pre-purchase authorization for a number of uses of said medical implement, and including information representing a status of said account in said compilation.

5. A method as claimed in claim 4 comprising automatically blocking said use of said medical implement by said customer if said information representing said status of said account indicates that said plurality of uses of said medical implement has been consumed.

6. A method as claimed in claim 1 comprising establishing an account between said customer and said vendor wherein said customer can pre-purchase use of said medical implement for a predetermined time duration, and including information representing a status of said time duration in said compilation.

7. A method as claimed in claim 6 comprising automatically blocking said use of said medical implement by said customer if said information representing said time duration indicates that said time duration has elapsed.

8. A method as claimed in claim 6 comprising monitoring elapsing of said time duration at said computer of said vendor.

9. A method as claimed in claim 1 comprising establishing a credit account between said customer and said vendor wherein said vendor extends credit to said customer for said use of said medical implement, and including information in said compilation representing a status of said credit account.

10. A method as claimed in claim 1 comprising periodically checking at said computer of said vendor, independently of said usage data, whether said economic status between said customer and said vendor exists permitting use of said medical implement, and if said economic status does not exist after a periodic check, automatically locking said use of said medical implement by said customer.

11. A method as claimed in claim 1 comprising the additional step of communicating payment data from said customer to said computer of said vendor for costs associated with said use of said medical implement and automatically crediting and account of said customer at said computer of said vendor for said payment.

12. A method as claimed in claim 11 comprising the additional step of after crediting said account of said customer for said payment, automatically communicating a receipt for said payment to said customer from said computer of said vendor.

13. A method as claimed in claim 1 wherein said communication between said computer of said medical implement and said computer of said vendor ensues via a communication network and wherein, upon a disruption of said communication network, repeatedly communicating said usage data from said computer of said medical implement to said computer of said vendor and repeatedly communicating said data for enabling or blocking said use of said medical implement by said customer from said computer of said vendor to said computer of said medical implement.

14. A method as claimed in claim 1 comprising communicating said usage data in a secure form selected from the group consisting of encryption and signing.

15. A method as claimed in claim 1 comprising communicating said data enabling or blocking said use of said medical implement by said customer in a secure form selected from the group consisting of encryption and signing.

16. A method as claimed in claim 1 comprising establishing a graduated cost schedule for said customer at said computer of said vendor for charging said customer for said use of said medical implement dependent on a degree of use by said customer of said medical implement.

17. A method as claimed in claim 1 comprising communicating examination-specific data, in addition to said usage data, from said computer of said medical implement to said computer of said vendor.

* * * * *